United States Patent [19]
Bae

[11] Patent Number: 5,972,815
[45] Date of Patent: Oct. 26, 1999

[54] BIOCERAMIC MATTER

[76] Inventor: Chang Soon Bae, #202, Tae Woo Villar, #64-11, Ju Am-Dong, Kwa, Chon-City, Kyong, Gi-Do, Rep. of Korea

[21] Appl. No.: 09/084,433

[22] Filed: May 27, 1998

[51] Int. Cl.$^6$ .................................................. C04B 35/00
[52] U.S. Cl. ................................ 501/1; 501/128; 501/154
[58] Field of Search .................................... 501/128, 154; 59/1

[56] References Cited

FOREIGN PATENT DOCUMENTS

| | | |
|---|---|---|
| 63-152465 | 6/1988 | Japan . |
| 06218280 | 8/1994 | Japan . |
| 07291654 | 11/1995 | Japan . |
| 09077620 | 3/1997 | Japan . |
| 09248519 | 9/1997 | Japan . |

*Primary Examiner*—Paul Marcantoni
*Attorney, Agent, or Firm*—Antonelli, Terry, Stout & Kraus, LLP

[57] ABSTRACT

There is disclosed a bioceramic matter as small in size as 300–475 mesh, comprising about 60.5–70.5% by weight of silica ($SiO_2$), about 10.7–13.7% by weight of alumina ($Al_2O_3$) and about 10.8–20.8% by weight of an effective-ingredient mix. The effecitive ingredient mix comprises about 1.4–3.4% by weight of ferric oxide ($Fe_2O_3$), about 0.3–0.7% by weight of magnesium oxide (MgO), about 0.8–1.6% by weight of calcium oxide (CaO), about 1.5–3.5% by weight of sodium oxide ($Na_2O$), about 0.4–2.4% by weight of potassium oxide ($K_2O$), about 0.09–0.1% by weight of phosphorous pentoxide ($P_2O_5$), about 0.02–0.2% by weight of titanium (Ti), about 0.02–0.2% by weight of manganese (Mn), about 0.02–0.2% by weight of selenium (Se), about 15–25 ppm of germanium (Ge), and about 2.5–3.5% by weight of silver (Ag). The bioceramic matter is so small that it can be subjected to a liquid phase under which it can form intermolecular bonds with other materials, and has excellent biological effects on organisms, including maintenance of freshness of foods, deodorization, vitalization, antibacterial activity, etc.

6 Claims, 1 Drawing Sheet

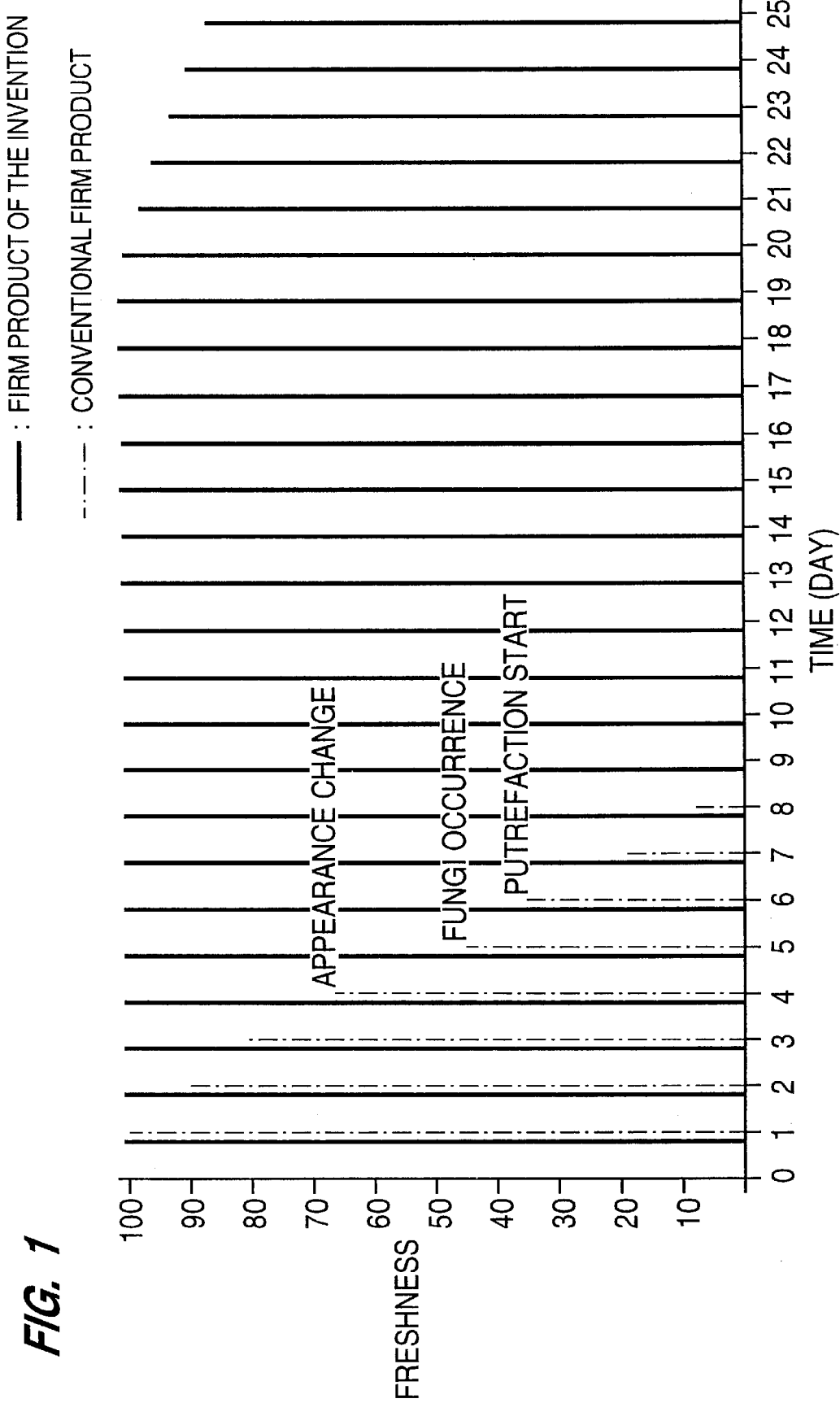

BIOCERAMIC MATTER

BACKGROUND OF THE INVENTION

1. Field of the Invention

The present invention relates, in general, to a bioceramic matter and, more particularly, to a bioceramic matter which is so small that it can be subjected to a liquid phase under which it can form intermolecular bonds with other materials, and which has excellent biological effects on organisms.

2. Description of the Prior Art

In 1800, Dr. F. W. Herschel of Great Britain found and reported to the academic world a wavelength ranging from 0.7 to 1000 microns, just beyond visible light, called Infrared, which has strong physical properties and great thermal activity. According to scientists, Infrared is classified into three types: Near-Infrared, Intermediate-Infrared and Far-Infrared. Far Infrared is the natural resonant frequency range of water and living organisms, including man. It is called the life force frequency. Now, Far Infrared is further utilized in Infrared photography, mapping the earth's surface, and guiding missiles to their target. Of Far Infrared frequencies, a wavelength range of 6–18 μm is well known to be beneficial to the human body by virtue of its activating and energizing effect on the body. Indeed, human skin radiates 9.36 microns Far Infrared wave which is very close to the resonant frequency of a water molecule—and rightly so since our bodies are about 70% water. In an aspect, Far Infrared waves are the safest and most beneficial energy source available.

Ceramics are refractory, inorganic, nonmetallic materials and were found to radiate a spectrum of Infrared waves. Ceramics offer many advantages compared to other materials. They are harder and stiffer than steel and more heat and corrosion resistant than metals or polymers while at the same time being less dense than most metals. Bioceramics are ceramics which radiate beneficial Infrared waves. Because of their advantages to human health, bioceramics are now used for various purposes including biomedicine and living necessaries. For instance, hard tissue replacements are very common in biomedicine. Bioceramic materials lend themselves to long-term hard tissue implants because of their remarkable chemical stability and inertness, mechanical strength, wear, corrosion resistance and biocompatibility. Another example includes vessels, clothes, and other living necessaries. These aim to utilize the physical properties of ceramics and the effects of the Infrared radiation emitted therefrom, including, for example, maintenance of freshness of foods, deodorization, vitalization, antibacterial activity, etc.

Recently, much study has been made on bioceramic materials. However, ceramic materials have not been developed without their being in solid states. When bioceramic materials in solid states are combined with other materials, e.g. resins, it is impossible to form molecular bonds therebetween. That is, the bioceramic materials of solid states are improper in making the films or synthetic resins which radiate the beneficial Infrared. For example, the films to which bioceramic materials in solid states are applied, if prepared, have not smooth surfaces. In addition, the prepared films are of low tensile strength so that they are apt to be torn. Thus, when foods, such as vegetables, fruits, fishes, meats, etc, are stored as wrapped by the films, the ability of the films to keep freshness is poor and their antibacterial activity, deodorization, and vitalization do no longer last as expected.

Bags made from synthetic polymers, e.g. polyethylene (hereinafter referred to as "polybags"), are now widely used to store foods. If polybags are prepared by thermally joining, for example, the polyethylene films containing the bioceramic material of solid states in order to provide the polybags with the effects the Far Infrared has on organisms, the thermal junctures of the polybags have a problem of leaking.

SUMMARY OF THE INVENTION

Therefore, it is an object of the invention to overcome the above problems encountered in prior arts and to provide a bioceramic matter which serves as an additive providing the effects Far Infrared waves have on organisms.

It is another object of the present invention to provide a bioceramic matter which is so small in size that it can be easily subjected to a liquid phase under which it can fuse with other materials.

In accordance with the present invention, the above object could be accomplished by a provision of a bioceramic matter as small in size as 300–475 mesh, comprising silica ($SiO_2$), alumina ($Al_2O_3$) and an effective-ingredient mix. The effective ingredient mix comprises ferric oxide ($Fe_2O_3$), magnesium oxide (MgO), calcium oxide (CaO), sodium oxide ($Na_2O$), potassium oxide ($K_2O$), phosphorous pentoxide $(PO_2)_5$ titanium (Ti), manganese (Mn), selenium (Se), germanium (Ge), and silver (Ag).

BRIEF DESCRIPTION OF THE DRAWING

FIG. 1 is a diagram showing a comparison of freshness between the organic materials stored in a conventional film product and in a film product of the invention.

DETAILED DESCRIPTION OF THE INVENTION

The biological effects of bioceramics are based on the fact that Far Infrared is the natural resonant frequency range of water and living organisms. Since a considerable part of living organisms consist of water, the resonant frequency of water molecules radiated from bioceramics can activate the water, affecting the living organisms. And, in the case of using a bioceramic material as an additive for providing the biological effects on living organisms, the additive must be compatible with the base materials and form intermolecular bonds with them. In this regard, additives and base materials are generally required to be in the phase under which both of them can be fused together.

Liquid phase is a convenient condition satisfying the fusion of different materials. Size is one of the most important factors in converting a material from solid phase to liquid phase. That is to say, the smaller a solid material is, the easier it can be subjected to a liquid phase.

Therefore, in one aspect of the present invention, the present invention pertains to a bioceramic matter which can serve as an additive providing the effects Far Infrared waves have on living organisms. The bioceramic matter of the invention comprises approximately 60.5–70.5% by weight of silica ($SiO_2$), approximately 10.7–13.7% by weight of alumina ($Al_2O_3$) and approximately 10.8–20.8% by weight of an effective-ingredient mix. The effective ingredient mix comprises approximately 1.4–3.4% by weight of ferric oxide ($Fe_2O_3$), approximately 0.3–0.7% by weight of magnesium oxide (MgO), approximately 0.8–1.6% by weight of calcium oxide (CaO), approximately 1.5–3.5% by weight of sodium oxide ($Na_2O$), approximately 0.4–2.4% by weight of potassium oxide ($K_2O$), approximately 0.09–0.1% by weight of phosphorous pentoxide ($P_2O_5$), approximately 0.02–0.2% by weight of titanium (Ti), approximately 0.02–0.2% by weight of manganese (Mn), approximately 0.02–0.2% by weight of selenium (Se), approximately 15–25 ppm of germanium (Ge), and approximately 2.5–3.5% by weight of silver (Ag).

Various tests showed the physical properties of the bioceramic matter as written in Table 1, below.

TABLE 1

| Properties | Values |
| --- | --- |
| Apparent Specific gravity | 2.64 |
| Void Volume (%) | 0.62 |
| Water Absorption (%) | 0.3 |
| Compressive strength (kg/cm$^2$) | 2100 |
| Far Infrared Radiation (%) | 95 |
| Deodorization (%) | 98 |
| Antibacterial Activity (%) | 42 |

In another aspect of the present invention, the present invention pertains to a bioceramic matter which is so small in size that it can be easily subjected to a liquid phase under which it can fuse with other materials. A bioceramic matter as small as 300–475 mesh can be applied for plastics, films and fibers because it forms intermolecular bonds with the base materials under one phase, e.g. liquid phase. After the addition of the bioceramic matter of the invention, films, plastics or fibers may be prepared in conventional methods.

A film was prepared from a composition comprising the bioceramic matter of the invention at an amount of 2–45% by weight and tested for physical properties. The results are given as shown in Table 2, below.

TABLE 2

| Tests | | Units | Values | Test Standards |
| --- | --- | --- | --- | --- |
| Tensile Strength | Width | Kg/cm$^2$ | 255 | KSM 3001-96 |
| | Length | Kg/cm$^2$ | 296 | |
| Elongation | Width | % | 715 | |
| | Length | % | 587 | |
| Thickness | Max. | mm | .050 | |
| | Min. | mm | .040 | |
| | Avg. | mm | .045 | |
| Tear Strength | Width | Kg/cm | 129 | |
| | Length | Kg/cm | 123 | |
| Stuff | Pd | ppm | N.D.* | ICP |
| | Cd | ppm | N.D. | |
| Erupts | Heavy Metals | ppm | <10 | Notification No. 95–47 of the Ministry of Health & Welfare of Korea |
| | Evp. Residues | ppm | .3 | |
| | KmnO$_4$ Cons. | ppm | .8 | |

*Not Detected.

The data of Table 2 show that the film is superior in tensile strength, draw ratio and tear strength, all. Particularly, neither Pd nor Cd is detected and heavy metals, evaporation residues and KMnO$_4$ consumption are each below their respective standards. In addition, the film has a smooth surface and is easy to thermally join to another film.

Resulting from the Far Infrared emitted from the bioceramic matter, the biological effects of the film on organisms were investigated. The biological effects are believed to be on the basis of the resonance between the vibration frequency of water molecule and the Far Infrared frequency. Activated water brings about growth promotion, freshness maintenance and antibacterial activity. Examples of the biological effects include the energizing of organic compounds, the activation of dissolved oxygen to restrain the infiltration of bacteria, and the anionization of air and the neutralization of cations to deodorize.

Bread, vegetables and roses were tested for freshness after each was put in a polybag made of the film. Referring to FIG. 1, there is shown the freshness. As seen in FIG. 1, for the organic materials in conventional polybags, appearance changed within 4 days, fungi occur within 5 days and putrefaction started within 6 days while the organic materials in the polybags of the invention maintained themselves at freshness 70 after 21 days and no change occurs even in appearance.

As described hereinbefore, the bioceramic matter of the present invention is made to a size as small as 300–475 mesh, so that it can be subjected to a liquid phase under which it forms intermolecular bonds with other materials, e.g. resins. Hence, the film or plastic products comprising the bioceramic matter of the invention are smooth and clear in surface and are easy to subject to thermal junction. The film products exhibit excellent physical properties including thermal resistance (980–1000° C.), tensile strength, elongation and tear strength and contain no harmful material to the human body. With these advantages, the film products of the invention have biological effects on organisms by activating water. Activated water brings growth of living organisms into promotion, foods into freshness, and bacteria into growth inhibition. Consequently, the film products prepared from the bioceramic matter of the invention provide biological effects, including the energizing of organic compounds, the activation of dissolved oxygen to restrain the infiltration of bacteria, and the anionization of air and the neutralization of cations to deodorize.

The present invention has been described in an illustrative manner, and it is to be understood the terminology used is intended to be in the nature of description rather than of limitation.

Many modifications and variations of the present invention are possible in light of the above teachings. Therefore, it is to be understood that within the scope of the appended claims, the invention may be practiced otherwise than as specifically described.

What is claimed is:

1. A bioceramic composition, comprising approximately 60.5–70.5% by weight of silica (SiO$_2$), approximately 10.7–13.7% by weight of alumina (Al$_2$O$_3$) and approximately 10.8–20.8% by weight of an ingredient mix comprising approximately 1.4–3.4% by weight of ferric oxide (Fe$_2$O$_3$), approximately 0.3–0.7% by weight of magnesium oxide (MgO), approximately 0.8–1.6% by weight of calcium oxide (CaO), approximately 1.5–3.5% by weight of sodium oxide (Na$_2$O), approximately 0.4–2.4% by weight of potassium oxide (K$_2$O), approximately 0.09–0.1% by weight of phosphorous pentoxide (P$_2$O$_5$), approximately 0.02–0.2% by weight of titanium (Ti), approximately 0.02–0.2% by weight of manganese (Mn), approximately 0.02–0.2% by weight of selenium (Se), approximately 15–25 ppm of germanium (Ge), and approximately 2.5–3.5% by weight of silver (Ag).

2. The bioceramic composition as set forth in claim 1, wherein the bioceramic composition has a particle size ranging from about 300 to 475 mesh.

3. The bioceramic composition according to claim 1, having the physical properties of apparent specific gravity 2.64, void volume 0.62%, water absorption 0.3%, compressive strength 2100 kg/cm$^2$, far infrared radiation 95%, deodorization 98% and antibacterial activity 42%.

4. The bioceramic composition according to claim 1, wherein said bioceramic composition is incorporated in a liquid phase.

5. A bioceramic composition, comprising approximately 60.5–70.5% by weight of silica (SiO$_2$), approximately 10.7–13.7% by weight of alumina ($Al_2O_3$) and approximately 10.8–20.8% by weight of an ingredient mix consisting essentially of approximately 1.4–3.4% by weight of ferric oxide ($Fe_2O_3$), approximately 0.3–0.7% by weight of magnesium oxide (MgO), approximately 0.8–1.6% by weight of calcium oxide (CaO), approximately 1.5–3.5% by weight of sodium oxide ($Na_2O$), approximately 0.4–2.4% by weight of potassium oxide ($K_2O$), approximately 0.09–0.1% by weight of phosphorous pentoxide ($P_2O_5$), approximately 0.02–0.2% by weight of titanium (Ti), approximately 0.02–0.2% by weight of manganese (Mn), approximately 0.02–0.2% by weight of selenium (Se), approximately 15–25 ppm of germanium (Ge), and approximately 2.5–3.5% by weight of silver (Ag).

6. A bioceramic composition, comprising approximately 60.5–70.5% by weight of silica ($SiO_2$), approximately 10.7–13.7% by weight of alumina ($Al_2O_3$) and approximately 10.8–20.8% by weight of an ingredient mix consisting of approximately 1.4–3.4% by weight of ferric oxide ($Fe_2O_3$), approximately 0.3–0.7% by weight of magnesium oxide (MgO), approximately 0.8–1.6% by weight of calcium oxide (CaO), approximately 1.5–3.5% by weight of sodium oxide ($Na_2O$), approximately 0.4–2.4% by weight of potassium oxide ($K_2O$), approximately 0.09–0.1% by weight of phosphorous pentoxide ($P_2O_5$), approximately 0.02–0.2% by weight of titanium (Ti), approximately 0.02–0.2% by weight of manganese (Mn), approximately 0.02–0.2% by weight of selenium (Se), approximately 15–25 ppm of germanium (Ge), and approximately 2.5–3.5% by weight of silver (Ag).

* * * * *